US00PP29734P2

(12) United States Plant Patent
Parks

(10) Patent No.: US PP29,734 P2
(45) Date of Patent: Oct. 9, 2018

(54) ***CAMELLIA* PLANT NAMED 'FALL FANTASY'**

(50) Latin Name: ***Camellia* hybrid**
Varietal Denomination: Fall Fantasy

(71) Applicant: Clifford Robert Parks, Chapel Hill, NC (US)

(72) Inventor: Clifford Robert Parks, Chapel Hill, NC (US)

(73) Assignee: David Parks, Chapel Hill, NC (US)

( * ) Notice: Subject to any disclaimer, the term of this patent is extended or adjusted under 35 U.S.C. 154(b) by 0 days.

(21) Appl. No.: 15/731,997

(22) Filed: Sep. 5, 2017

(51) Int. Cl.
*A01H 5/00* (2018.01)

(52) U.S. Cl.
USPC ..... Plt./245

(58) Field of Classification Search
USPC ..... Plt./245
See application file for complete search history.

*Primary Examiner* — Annette H Para
(74) *Attorney, Agent, or Firm* — Penny J. Aguirre

(57) ABSTRACT

A new cultivar of *Camellia* named 'Fall Fantasy' that is characterized by its very floriferous blooming habit, its infloresences with a double rose form, its upright and dense growth habit making it suitable for use as a screening plant, and its rapid growth habit and ease of propagation.

2 Drawing Sheets

Botanical classification: *Camellia* hybrid.
Variety denomination: 'Fall Fantasy'.

BACKGROUND OF THE INVENTION

The present invention relates to a new and distinct cultivar of *Camellia* plant, botanically of hybrid origin and known as *Camellia* 'Fall Fantasy'. The new cultivar will be referred to hereafter by its cultivar name, 'Fall Fantasy'. 'Fall Fantasy' is a new perennial shrub grown for container and landscape use.

'Fall Fantasy' was derived from an ongoing breeding program conducted by the Inventor in Chapel Hill, N.C. The objectives of the breeding program are to develop new cultivars of *Camellia* with improved cold hardiness, floriferous blooming habits, improved flower quality, and extended bloom periods. The Inventor made a controlled cross in 1992 in Chapel Hill, N.C. between *Camellia sasanqua* 'Wm. Lanier Hunt' (not patented) as the female parent and *Camellia* 'Snow Flurry' (not patented) as the male parent. 'Fall Fantasy' was selected in 2002 as a single unique plant amongst the resulting seedlings.

Asexual propagaton of the new cultivar was first accomplished by stem cuttings by the Inventor in 2003 in Chapel Hill, N.C. Asexual propagation by stem cutting has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Fall Fantasy' as a unique cultivar of *Camellia*.

1. 'Fall Fantasy' exhibits a very floriferous blooming habit.
2. 'Fall Fantasy' exhibits infloresences with a rose form double flowers.
3. 'Fall Fantasy' exhibits an upright and dense growth habit making it suitable for use as a screening plant.

4. 'Fall Fantasy' exhibits a rapid growth habit and is readily propagated for easy production.

The female parent of 'Fall Fantasy', 'Wm. Lanier Hunt', differs from 'Fall Fantasy' in having flowers that are darker pink in color, flowers that are peony in form, a spreading plant habit and fewer blooms. The male parent of 'Fall Fantasy', 'Snow Flurry', differs from 'Fall Fantasy' in having flowers that are white in color, flowers that are peony in form, a spreading growth habit, earlier blooming season and leaves that are more narrower and longer. 'Fall Fantasy' can also be compared to the *Camellia sasanqua* cultivars 'Susy Dirr' (U.S. Plant Pat. No. 24,888) and 'Lisa' (not patented). 'Susy Dirr' is similar to 'Fall Fantasy' in having a vigorous growth habit and in flower color and form. 'Susy Dirr' differs from 'Fall Fantasy' in having a less floriferous blooming habit and a loose and less dense plant habit. 'Lisa' is similar to 'Fall Fantasy' in having flowers that are rose in form that appear formal double as it opens. 'Lisa' differs from 'Fall Fantasy' in being less vigorous and less floriferous and in having a spreading plant habit and flowers that are darker pink in color.

BRIEF DESCRIPTION OF THE DRAWINGS

The accompanying colored photographs illustrate the overall appearance and distinct characteristics of the new *Camellia*. The photographs were taken of a plant of 'Fall Fantasy' about 1.5 years in age as grown outdoors in a two-quart container in Chapel Hill, N.C.

The photograph in FIG. 1 provides a side-view of 'Fall Fantasy' in bloom.

Figure 1:
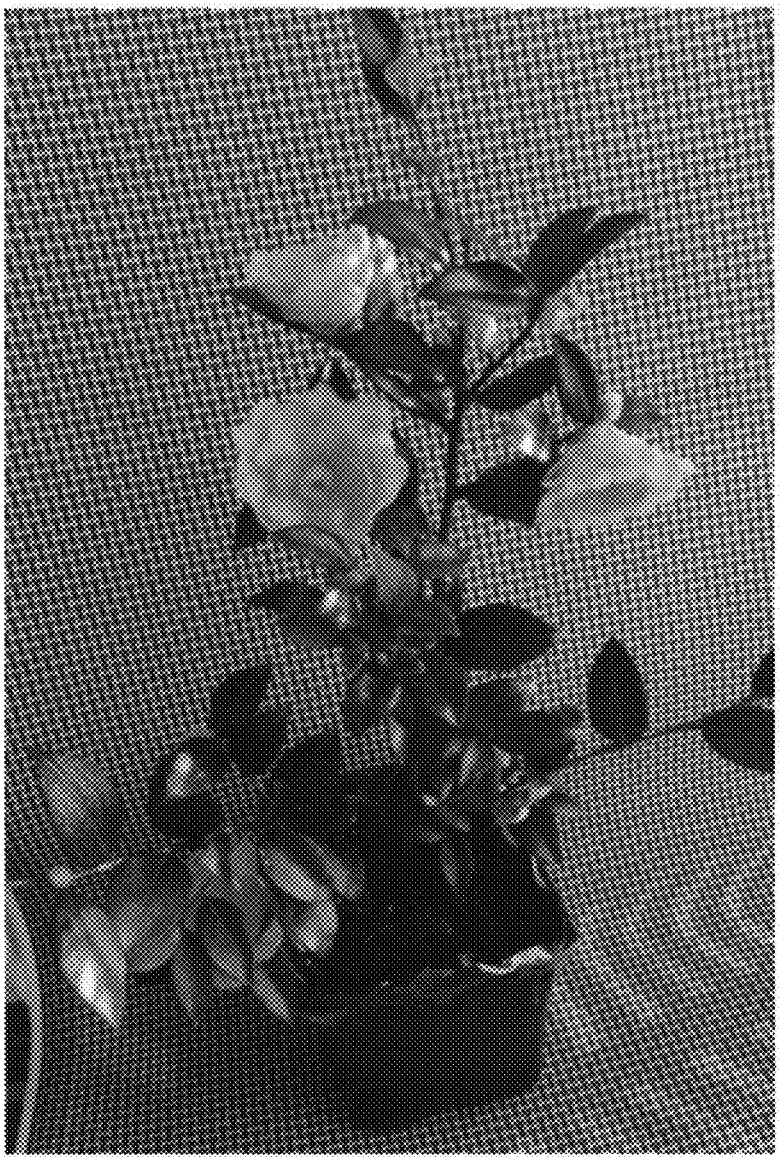
Figure 2:
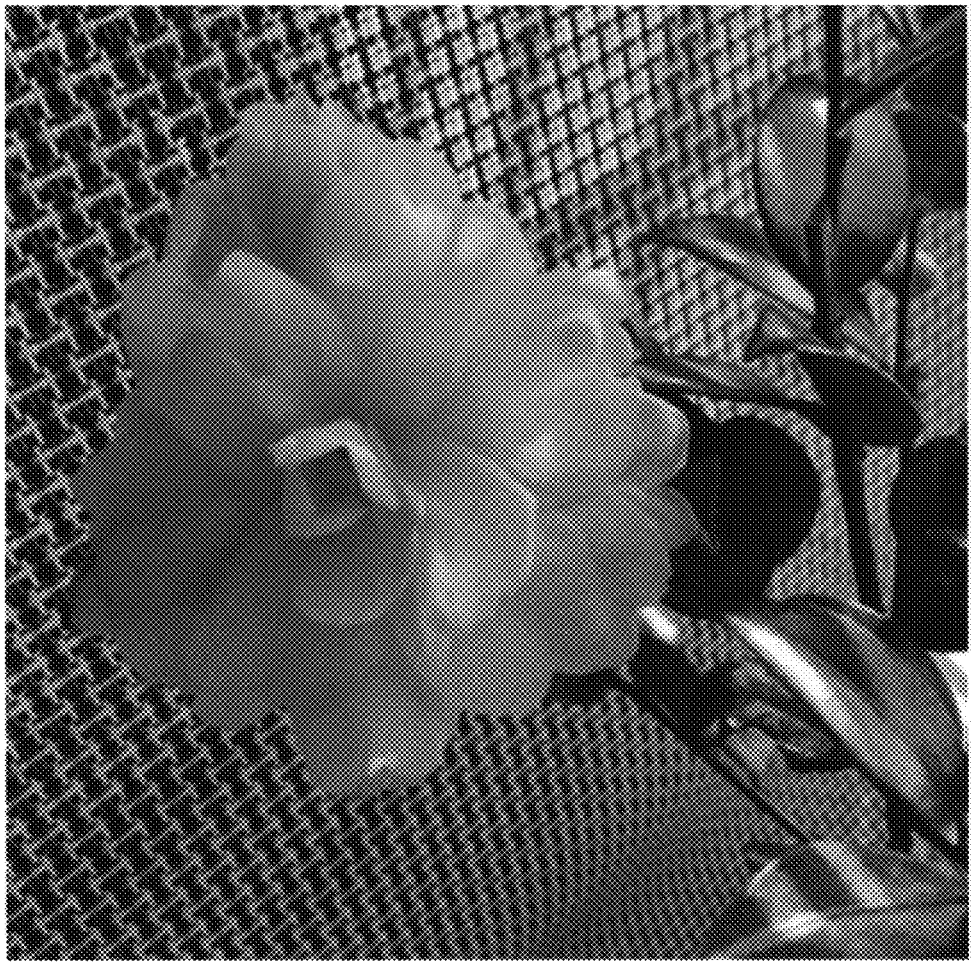

The photograph in FIG. 2 provides a close-up view of a flower of 'Fall Fantasy'.

The colors in the photographs are as close as possible with digital photography techniques available, the color values cited in the detailed botanical description accurately describe the colors of the new *Camellia*.

DETAILED BOTANICAL DESCRIPTION

The following is a detailed description of plants about 1.5 years in age as grown outdoors in 2-quart containers in Chapel Hill, N.C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—3 to 4 weeks in November in central North Carolina.

*Plant type.*—Evergreen shrub.

*Plant habit.*—Upright and dense.

*Height and spread.*—An average of 3 m in height and 1.5 m in spread when mature in the landscape as a ten year-old plant.

*Cold hardiness.*—At least hardy in U.S.D.A. Zone 7.

*Diseases and pests.*—No resistance or susceptibility to diseases or pests have been observed.

*Propagation.*—Stem cuttings.

*Time required for root initiation.*—An average of 4 to 6 weeks.

*Time required for root development.*—About 4 to 6 months to fully develop as a young plant.

*Growth rate.*—Vigorous.

Branch description:

*Stem shape.*—Round.

*Stem strength.*—Strong.

*Stem color.*—Newer growth; 174A, mature branches; a blend of 200A and 200D.

*Stem size.*—Main lateral branches; an average of 30 cm in length and 5.5 mm in width (mid stem) with secondary lateral branches up to 21 cm in length and an average of 3 mm in width, and tertiary branches an average of 5 mm in length and 1.5 mm in wdth.

*Stem surface.*—Young; finely barked and sparsely covered with soft pubescent hairs, mature; finely barked, slightly rough to touch.

*Branching.*—1 main lateral branch, an average of 9 secondary branches and up to 3 terminal branches per secondary branch, secondary and tietiary branches held at about a 30° angle.

Foliage description:

*Leaf shape.*—Elliptic.

*Leaf division.*—Simple.

*Leaf base.*—Broadly cuneate to rounded.

*Leaf apex.*—Bluntly acuminate to acute.

*Leaf fragrance.*—None.

*Leaf margins.*—Serrate.

*Leaf arrangement.*—Alternate.

*Leaf attachment.*—Petiolate.

*Leaf substance.*—Thick and rubbery.

*Leaf surface.*—Upper and lower surface; smooth, glabrous and glossy.

*Leaf size.*—An average of 5.5 cm in length and 2.8 cm in width.

*Leaf quantity.*—An average of 15 per branch 21 cm in length.

*Leaf venation.*—Pinnate, inconspicuous except for mid rib; upper surface 146B in color, lower surface 146C in color.

*Leaf color.*—Young leaves upper surface; 146A, young leaves lower surface; 146B, mature leaves upper surface; NN137A, mature leaves lower surface; a color between 144A and 138A.

*Petioles.*—Flattened in shape, an average of 2 mm in width and 5 mm in length, glabrous surface, 146B in color, strong and heald at a 15° upwards to stem.

*Stipules.*—None.

Inflorescence description:

*Inflorescence type.*—Solitary at terminus of lateral branches.

*Flower number.*—6 to 8 per lateral stem (1 to 2 per secondary branch).

*Flower fragrance.*—Slight herbacous scent.

*Flower longevity.*—About one week, self cleaning.

*Flower type.*—Rose form double (according to the American *Camellia* Society rules).

*Flower aspect.*—Upright to slightly outward.

*Flower size.*—An average of 8 cm in diameter and 4.5 cm in depth.

*Peduncles.*—None, flowers are sessile to stem.

*Flower buds.*—Ovate in shape, an average of 2.5 cm in length and 1.5 cm in width, color; 145B and 145C on sepal portion, a blend of 68B and 68C on petal portion, surface pubescent on sepal portion and glabrous on petal portion.

*Sepals.*—An average of 6, irregularly round in shape and strongly cupped inward, imbricate, an average of 1 cm in length and width, rounded apex, truncate base, entire margin with slightly flattened edges, color inner and outer surface; a blend of 145A and 138B, outer surface covered with silky hairs, inner surface glabrous and satiny.

*Petals.*—An average of 27, ovate-oblong in shape, an average of 3.5 cm in length and 3 cm width, margins entire, base cuneate, apex rounded with single notch (cordate-like), color outer and lower surfaces when opening; a blend of 68B and 68C, color upper and lower surfaces when fully open; a blend of 65A, 65B, and 65C, with center of the base suffused with 26C, glabrous texture on inner and outer surface.

*Petaloids.*—3 to 4, irregular in shape an apex, an average of 5 mm in length and 3 mm in width, base cuneate, apex rounded, and same surface, margins, and coloration as petals.

Reproductive organs:

*Pistil.*—Average of 3, style is an average of 5 mm in length, 2 mm in width and 145C in color, stigmas are tri-parted with each appendage <0.5 mm in diameter, club-shaped, 145B in color and glandular in appearance, ovary is oblong-oval in shape, imbricate surface, and 155A in color.

*Stamens.*—An average of 4 fully formed, filaments; an average of 4.5 mm in length, 5C in color, anthers; an average of 3 mm in length and 14B in color with 2 petal-like wings at apex; color 14D with centers 68A, 1 mm in length and width, ovate in shape, pollen; none observed.

*Fruit and seed.*—None have been oberved to date.

It is claimed:

1. A new and distinct cultivar of *Camellia* plant named 'Fall Fantasy' as herein illustrated and described.

* * * * *